United States Patent
Carlson et al.

(10) Patent No.: US 10,201,458 B2
(45) Date of Patent: Feb. 12, 2019

(54) METHOD FOR PRODUCING PANT-TYPE ARTICLES HAVING A CHASSIS STRUCTURE AND PANT-TYPE ARTICLES PRODUCED ACCORDING TO THE METHOD

(75) Inventors: Ulrika Carlson, Billdal (SE); Hans Een, Mölnlycke (SE); Margareta Wennerbäck, Mölnlycke (SE)

(73) Assignee: ESSITY HYGEINE AND HEALTH AKTIEBOLAG, Göteborg (SE)

(*) Notice: Subject to any disclaimer, the term of this patent is extended or adjusted under 35 U.S.C. 154(b) by 1349 days.

(21) Appl. No.: 13/127,139

(22) PCT Filed: Nov. 3, 2008

(86) PCT No.: PCT/SE2008/051253
§ 371 (c)(1),
(2), (4) Date: May 2, 2011

(87) PCT Pub. No.: WO2010/050867
PCT Pub. Date: May 6, 2010

(65) Prior Publication Data
US 2011/0209270 A1    Sep. 1, 2011

(51) Int. Cl.
*A41B 9/00* (2006.01)
*A61F 13/15* (2006.01)

(52) U.S. Cl.
CPC .. *A61F 13/15593* (2013.01); *A61F 13/15804* (2013.01); *B32B 2309/14* (2013.01); *B32B 2555/02* (2013.01)

(58) Field of Classification Search
CPC ......... A61F 13/15593; A61F 13/15804; B32B 2309/14; B32B 2555/02
(Continued)

(56) References Cited

U.S. PATENT DOCUMENTS 4,655,760 A    4/1987    Morman et al.
4,657,802 A    4/1987    Morman
(Continued)

FOREIGN PATENT DOCUMENTS

EP    0217032 B1    2/1992
EP    0 714 351     12/1998
(Continued)

OTHER PUBLICATIONS

David R. Roisum, "The Mechanics of Web Handling," Chapter 4, pp. 49-51, 1998, TAPPI Press.
(Continued)

*Primary Examiner* — Michael N Orlando
*Assistant Examiner* — Marta S Dulko
(74) *Attorney, Agent, or Firm* — Drinker Biddle & Reath LLP

(57) ABSTRACT

A method for producing pant-type articles having a waist-encircling portion and leg-encircling portions. The method includes forming a chassis structure and at least one elastic panel being formed by providing a first web, which is an elastic web including at least one layer of an elastic material. The first web is stretched at least 70% in at least one direction. The stretched first web is bonded while the first web is held in the stretched state to a second web. The second web includes at least one layer of an elastic or non-elastic material, and the bonded first and second webs form an elastic composite web. The elastic composite is relaxed in the at least one direction by at least 4% of the stretched length of the stretched first web. The chassis structure is assembled from chassis components including the stretched and relaxed composite web.

26 Claims, 6 Drawing Sheets

(58) Field of Classification Search
USPC ......................................................... 156/229
See application file for complete search history.

(56) References Cited

U.S. PATENT DOCUMENTS

| | | | |
|---|---|---|---|
| 5,143,679 | A | 9/1992 | Weber et al. |
| 5,156,793 | A | 10/1992 | Buell et al. |
| 5,167,897 | A | 12/1992 | Weber et al. |
| 5,422,172 | A | 6/1995 | Wu |
| 5,576,090 | A | 11/1996 | Suzuki |
| 5,592,690 | A | 1/1997 | Wu |
| 5,634,216 | A | 6/1997 | Wu |
| 5,733,628 | A | 3/1998 | Pelkie |
| 5,861,074 | A | 1/1999 | Wu |
| 6,964,720 | B2 * | 11/2005 | Schneider et al. ............ 156/161 |
| 2004/0102754 | A1 | 5/2004 | Morman et al. |
| 2006/0148354 | A1 | 7/2006 | Shelley et al. |
| 2009/0038751 | A1 * | 2/2009 | Hermansson et al. ........ 156/269 |

FOREIGN PATENT DOCUMENTS

| | | |
|---|---|---|
| JP | 62-033889 | 2/1987 |
| JP | 62033889 | 2/1987 |
| JP | 2007105453 | 4/2007 |
| JP | 2007105453 A | 4/2007 |
| WO | 03/047488 | 6/2003 |
| WO | 2004/078083 | 9/2004 |
| WO | 2006/036090 | 4/2006 |
| WO | 2007/133127 | 11/2007 |
| WO | 2007/133146 | 11/2007 |
| WO | 2007/138373 | 12/2007 |
| WO | WO-2008/026106 A2 | 3/2008 |
| WO | 2008/079061 | 7/2008 |

OTHER PUBLICATIONS

Opposition to European Patent No. EP 2344104 B1 filed Mar. 18, 2016 in European Patent Application No. 08877830.3.

* cited by examiner

METHOD FOR PRODUCING PANT-TYPE ARTICLES HAVING A CHASSIS STRUCTURE AND PANT-TYPE ARTICLES PRODUCED ACCORDING TO THE METHOD

CROSS-REFERENCE TO PRIOR APPLICATION

This application is a § 371 National Stage Application of PCT International Application No. PCT/SE2008/051253 filed Nov. 3, 2008.

FIELD OF THE INVENTION

The disclosure pertains to a method for producing pant-type articles, such as pant type disposable absorbent articles, each article including a chassis structure having at least one elastic panel. The disclosure also relates to a pant-type article produced according to the disclosed method.

BACKGROUND

Pant-type hygienic articles include a pant-shaped chassis structure and optionally an absorbent core component integrated with the chassis. A major objective when designing pant articles is to make them resemble ordinary underwear as closely as possible. Hence, absorbent articles such as pant diapers, sanitary pants and incontinence pants are designed to fit comfortably and snugly about the wearer. It is also necessary that the absorbent articles provide sealing against leakage of body fluids out of the absorbent article without being so tight that they are uncomfortable to wear. It is further desirable that the articles are capable of being pulled up and down over the hips of the wearer in the manner of a pair of underpants to allow the wearer or caregiver to easily remove a soiled article and to replace it with a new clean article. For all of these reasons, the article chassis is usually made of a material that is elastically stretchable, at least in the areas intended to be applied over the wearer's hips. Furthermore, it is desirable that the chassis surrounding the absorbent parts of the pant article is permeable to air and vapor, i.e. that it is breathable. A breathable article prevents moisture from remaining on the skin of the wearer and is more comfortable and less warm to wear than a non-breathable article. It is also beneficial if the article is soft, smooth and textile-like, so that it does not chafe the skin of the wearer and so that it resembles ordinary underwear as closely as possible.

One type of elastic material for pant articles is a laminate including an elastic film sandwiched between two layers of non-elastic nonwoven material. In order to render the laminate elastically stretchable, it is subjected to an activation treatment. A three-layer, activated laminate is disclosed in International Patent Application No. WO 03/047488. The activated laminate is produced by incrementally stretching an elastic film layer between two non-elastic cloth-like layers. Incremental stretching is carried out by passing the laminate between intermeshing gear rollers. Activation of first elastic laminates by incremental stretching is also disclosed in U.S. Pat. Nos. 5,143,679, 5,156,793 5,167,897, 5,422,172, 5,592,690, 5,634,216 and 5,861,074. The non-elastic cloth-like layers are fully or partially broken or torn during the activation process so that the elasticity of the laminate after activation is governed mainly by the elasticity of the elastic film layer. In the three-layer laminate in WO 03/047488, the non-elastic layers are completely broken so that the elasticity of the activated laminate is substantially the same as the elasticity of the elastic film layer.

The disclosed laminates have excellent comfort characteristics and are soft, flexible, breathable and elastic. However, a major disadvantage with the three-layer laminates disclosed in WO 03/047488 is that the activation process at least partially breaks and destroys the cloth-like layers resulting in a material having decreased tensile strength and puncture resistance in a direction perpendicular to the direction of elasticity of the material. When used as a chassis component in a disposable pant article, the material is easily torn when exposed to the forces arising when putting on or pulling off the pant article. This tearing problem is particularly pronounced for female wearers or caregivers who often have long fingernails that may penetrate and tear the pant material.

Another problem with three-layer laminates in WO 03/047488 is that they have a pre-determined extensibility and elasticity. However, it is often desirable to have different elasticity in different parts of a pant-type article. In order to accomplish this, it is necessary to supplement the elastic panels created from the three-layer laminate with additional elastic elements or to make different parts of the diaper chassis from different laminates. All such extra components are costly and complicate the manufacturing process since they require additional process steps, thus incurring additional processing costs.

In order to remedy the shortcomings of the laminated elastic materials according to WO 03/047488, it has been proposed in WO 2007/133146 to produce a three-layer elastic laminate in a two-step process. The two-step process involves producing a two-layer laminate comprising a non-elastic fibrous nonwoven web and an elastic film. The two-layer laminate is activated by incremental stretching in at least one direction to render the two-layer laminate elastically stretchable. The two-layer laminate is subsequently stretched by 35-200% in at least one direction, the degree of stretching determining the elasticity of the final three-layer laminate. The stretched two-layer laminate is then used in a pant-forming process to create one or more elastic panels in the chassis structure of a pant-type absorbent article by laminating the elastic film of the stretched two-layer laminate to a nonwoven chassis component.

It has been discovered that elastic webs such as the laminates disclosed in WO 03/047488 and in WO 2007/133146 are difficult to process in fast-running machines producing disposable absorbent articles. As a result of necking, the activated and stretched elastic webs tend to curl at the edges, implying that they are difficult to incorporate into high-speed production processes.

A further problem is that the extensibility of the elastic panels in the finished absorbent articles is less than would be expected, implying that the articles will fit only wearers within a limited size range.

SUMMARY

It is desired to provide an improved method for producing an absorbent article having at least one elastically stretchable panel. The absorbent article desirably also has improved fit and is useful over a greater range of wearer sizes and body shapes.

In a first aspect, there is provided a method for producing pant-type articles having a waist-encircling portion and leg-encircling portions, each article including a chassis structure having at least one elastic panel. The method includes forming the chassis structure, where the at least one elastic panel is formed by:

a) providing a first web, which is an elastic web including at least one layer of an elastic material;
b) stretching the first web by at least 50% in at least one direction,
c) bonding the stretched first web while the first web is held in the stretched state to a second web, the second web including at least one layer of an elastic or non-elastic material, the bonded first and second webs forming an elastic composite web,
d) relaxing the elastic composite in the at least one direction by at least 4% of the stretched length of the stretched first web,
e) assembling the chassis structure from chassis components including the stretched and relaxed composite web (4).

In a particular embodiment, the partially relaxed composite elastic web is produced in-line with the pant-forming process, the relaxed composite web being directly introduced in the pant-forming process and joined to further components without any interruption in the process between the partial relaxation and further process steps. Accordingly, the composite web will be incorporated into the chassis structure with a remaining stretch.

The first web may be stretched by at least 70% of the initial non-stretched length, preferably by at least 90% of the initial non-stretched length. The maximum stretch that the first web may be subjected to is determined by the properties of the particular elastic material that is used. In a particular embodiment, the first web is stretched as much as the material will allow without rupturing and without loosing its elastic properties. The first web may be stretched by up to 150% of the initial non-stretched length, preferably by up to 300% of the initial non-stretched length and most preferably by up to 500% of the initial non-stretched length.

The stretched composite elastic web may be relaxed by 4-50% of the stretched length of the first elastic web, preferably by 4-20% of the stretched length of the first elastic web and most preferably by 4-10% of the stretched length of the first elastic web.

In a certain embodiment, the method is performed as a continuous process. The relaxed elastic composite web is introduced directly in-line into the pant-forming process and, in more certain embodiments, is joined to other components in a continuously running chassis web travelling in a machine direction (MD). In a particular embodiment of a continuous process, the stretched first elastic web is stretched at least in the MD and the subsequent relaxation of the bonded composite elastic web is then also performed in the MD.

A web of material as used herein is any generally two-dimensional, flexible material or combination of materials such as plastic films, nonwovens, foams or textiles. The web may be a multicomponent web including several layers and/or areas of different materials. A web as used herein may be in the form of a continuous web or in the form of a discreet web.

A compound chassis web as used herein is a continuous web including multiple components. A compound chassis web is formed as soon as at least two components are joined together in a continuous web of materials. In an assembled compound chassis web, all the chassis components have been joined so that the compound chassis web is a continuous web of connected individual chassis blanks which are then converted into individual chassis structures. The assembled compound chassis web is cut to form leg openings. The web is folded and side joins are formed in the folded web between chassis blanks each chassis blank optionally carrying an integrated core component. Individual pant-type articles are then separated from the compound chassis web by severing the web at the side joins. Usually the severing step is performed by cutting between two parallel bond lines forming the side seams and being arranged at a small distance from each other in the cross machine direction (CD) of the compound chassis web. The side seams may be formed as one single broad bond line which is cut in two in the severing step. Further ways of forming side seams in a pant-type absorbent article is disclosed in WO 2007/138373 and WO 2008/079061.

In a particular embodiment of the method, the relaxed composite elastic web is in the form of a continuously running web that is introduced in-line into the production process as a component in a continuous compound chassis web including further components of the pant-type article such as an outer cover layer, an inner cover layer, an absorbent core, elastic elements, fasteners, size tags, etc. The elastic panel may be a front panel, a rear panel, a waist panel, or a side panel in the pant-type article. The composite elastic web is a laminate of at least one elastic layer with one or more additional layers. The elastic layer or layers may be elastic film or elastic nonwoven or combinations thereof. Particular composite elastic webs are three-layer nonwoven-film-nonwoven laminates as disclosed herein. In a pant-type article including several elastic panels, different materials may be chosen for the different panels. The materials may differ in composition, thickness, elastic properties, breathability, stiffness, drapability, etc.

One example of useful three-layer laminates are those produced in the two-step process disclosed in WO 2007/133146 as these laminates are conformable and highly breathable and combine high wearer comfort and tensile strength with good production economy. Other three layer laminates that may be used are those disclosed in WO 03/047488.

The stretched and relaxed composite elastic webs can be used to create elastic panels having different extensibility, flexibility and elasticity. This can be achieved by selecting different elastic materials and by subjecting the elastic material in the webs to different degrees of stretching and relaxation.

As used herein, an elastic material is a material having a permanent elongation after relaxation of less than 10% after the material has been subjected to an elongation of 30% in the elasticity test specified in the description.

A non-elastic material is a material that does not fall within the definition of an elastic material. Accordingly, a non-elastic material as used herein is a material that may be stretchable or non-stretchable. In the case of a stretchable material, the material has a permanent elongation after stretching and relaxation of more than 10% after having been subjected to an elongation of 30% as determined according to the elasticity test specified in the description.

In particular embodiments, when the stretched and relaxed composite elastic web is an elastic film laminate, the elastic film is perforated in order to render the laminate breathable. This can be achieved directly in conjunction with the lamination process if, for instance, a nonwoven web is bonded to the elastic film by extrusion coating. The perforating step can be carried out by passing the combined elastic layer and nonwoven web over a vacuum lamination drum while the elastic layer is in a molten or semi-molten state. Such a process is disclosed in U.S. Pat. No. 5,733,628 and results in the elastic film being formed into a three-dimensional apertured laminate layer.

An elastic laminate may be coperforated by any suitable perforation method such as perforation with heated needles, punching, perf-embossing or ultrasonic perforation.

The elastic film can be a prefabricated perforated film that is bonded to a nonwoven web by any suitable means such as adhesively, thermally or with ultrasonic welding.

When using stretch-activated elastic laminates such as disclosed in WO 03/047488 and WO 2007/133146, the activation step involves incremental stretching of the first elastic laminate so that the non-elastic web is broken or torn, at least partially. Activation can be carried out by heated or non-heated intermeshing gear rollers having circumferentially arranged teeth that intermesh and thereby stretch the laminate. The activation step allows the laminate to be subsequently stretched without being appreciably restrained by the nonwoven web. The degree of breaking of the nonwoven material determines the maximum possible elongation for the resulting laminate. If the nonwoven material is completely broken in the activation process, the laminate will have substantially the same maximum elongation as the elastic film layer.

It is also possible to use other types of stretch-bonded laminates involving minimal tearing or breaking of the fibers in the nonwoven layer or layers comprised in the laminates.

The amount of stretching of the first elastic web is specified as a percentage of the initial, non-stretched length of the first elastic web in the direction of stretch. By way of example, a first elastic web having a first, non-stretched length of 1 m and being stretched by 50% has a second, stretched length of 1.5 m. Accordingly, the stretched length is the complete length in the stretched state of the web.

After the stretching step, the first elastic web is bonded to a second web and the thus formed elastic composite is relaxed in the direction of stretch by at least 4% of the stretched length. By way of example, a first elastic web that initially has a length in the direction of stretch of 350 mm and which is then stretched by 95% to 682 mm, bonded to a second web and subsequently relaxed together with the second web by 5.4% to 647 mm has a remaining stretch of 85% of the non-stretched length of the first elastic web when it is subsequently used to form a chassis structure in a pant-type article.

The relaxation step eliminates or at least considerably reduces the tendency of the composite elastic web to curl at the edges which is a particular problem when the first elastic web has been stretched over the limit where the stretching causes the width of the web to be reduced, a phenomenon that is known as "necking". By means of the relaxation step, it is possible to produce composite elastic webs in-line with the rest of the process and at the high production speeds required for the manufacturing of disposable articles.

It has also been surprisingly found that the relaxation step considerably improves the elastic characteristics of the elastic composites when used to form elastic panels in a pant-type article. The pant-type articles produced by the disclosed methods can be used by wearers throughout a broader range of sizes and body shapes than articles produced without the relaxation step. The articles will also have higher conformability and will adapt to the shape of users of different body shapes. Hence, the articles will readily conform to the round bellies of infants while maintaining a close fit over the hips and buttocks. The pant-type articles produced provide excellent fit and conformability also for adult wearers who may have the same panty size but still differ greatly in body shape. The articles will fit wearers having a straight figure as well as wearers having a protruding belly, broad hips, a narrow waist, etc. The articles will also accommodate the usual variations in waist circumference that occur during the day for one and the same wearer.

A relaxed elastic composite web or a stretched and relaxed elastic composite web as used herein comprises a web that has first been stretched in at least one direction by at least 50% of the initial non-stretched length, preferably stretched by at least 70% of the initial non-stretched length, and most preferably stretched by at least 90% of the initial non-stretched length. The web may have been stretched by up to 150% of the initial non-stretched length, preferably by up to 300% of the initial non-stretched length and most preferably by up to 500% of the initial non-stretched length. The stretched elastic first web has been bonded to a second web while in the stretched state and has subsequently been relaxed by at least 4% of the stretched length of the first elastic web, preferably relaxed by 4-50% of the stretched length of the first elastic web, more preferably by 4-20% of the stretched length of the first web and most preferably by 4-10% of the stretched length of the first web.

The stretched and partially relaxed composite elastic web has a remaining stretch of at least 25% of the initial non-stretched length of the first elastic web when the composite web is subsequently joined in-line with other components in the process as disclosed.

A completely relaxed web is a web upon which no external forces are acting. External forces are those forces that are applied to the web during production and when putting on and wearing the absorbent article. The stretched and partially relaxed composite elastic web produced in-line in the disclosed process is not completely relaxed when being incorporated into the compound chassis web but retains a degree of stretch after the relaxation step.

A laminate as used herein is a material web including at least two different and distinct layers that have overlapping parts, the overlapping parts being bonded together to form the laminate.

A pant-type absorbent article as used herein is an absorbent garment that is configured to fit a wearer as a pair of underpants, implying that the absorbent article includes side seams at the waist-encircling portion of each article and that the article has a waist opening and two leg openings. Usually the side seams are formed in the chassis structure after any other production steps have been performed such as after the application of one or more optional features such as leg elastic, waist elastic, inner raised barriers, size tags, absorbent components, topsheet layers, barrier layers, reinforcements, patches, etc. Side seams may be formed in any suitable manner such as adhesively, or by heat or ultrasonic welding. In a particular embodiment, the side seams are made to be openable side seams implying that the side seams are strong enough to withstand the pulling and stretching forces applied to the side seams when putting on and wearing the pant-type article but may be broken without undue tearing of the article when the article is being removed from the wearer. Openable side seams may be pealable side seams or may have been made openable by arranging tear strips, perforations, or other types of weakenings along the side seams. The openable side seams may be reclosable to allow inspection. Usually, the side seams are arranged to be placed at the wearer's hips when the pants are worn, but the side seams can also be arranged more to the front of the pants. In certain embodiments, the side seams are designed so that they can withstand the tensile forces which arise when the article is being put on and is being worn, but such that they can be torn apart or opened in a controlled manner when the pants are taken off or to check if an absorbent pant-type article needs changing.

A pant-type article having openable side seams may be provided with fasteners in order to provide reclosability of the side seams. The fasteners may be mating fasteners commonly used in the art such as hook-and-loop fasteners, adhesive fasteners mating with a landing member, press-studs, etc. In particular embodiments, the mating fasteners are reclosable fasteners so that the article can be repeatedly opened and reclosed for inspection and for readjustment of the fit.

An absorbent core component can be placed on a compound chassis web with a central portion extending over a central nonwoven chassis web and with end portions of the core component extending in over elastic panel webs arranged along the edges of the central nonwoven chassis web. The absorbent core component can be integrated with the chassis web at any point in the production process.

The stretching of the elastic panel web may be performed in more than one step. Similarly, relaxation of the stretched elastic panel web may be performed in at least two steps.

In another aspect, an article may be produced by:
a) joining a first relaxed elastic composite web to a first edge of a continuous central nonwoven chassis web, which is a component of the compound chassis web, and
b) joining a second relaxed elastic composite web to a second edge of the continuous central nonwoven chassis web.

The first composite elastic web may be stretched to a greater degree than the second composite elastic web.

In yet another aspect, an article may be produced by:
a) laminating a first stretched elastic web to a first edge portion of a continuous nonwoven web,
b) laminating a second stretched elastic web to a second edge portion of the continuous nonwoven web,
c) relaxing the composite elastic web formed by laminating the first and second stretched elastic webs to the continuous central nonwoven chassis web by at least 4% of the stretched length of at least one of the stretched elastic webs.

The first stretched elastic web may be stretched to a greater degree than the second stretched elastic web.

Joining of the webs may be made by any suitable method such as adhesively, by ultrasonic welding, thermowelding, stitching, etc.

The articles formed by joining elastic webs to a central chassis web are produced in a cross-machine direction (CD) which means that the articles are arranged along the compound chassis web with the longitudinal direction of each article arranged in the CD so that the waist borders of the articles form the MD side edges of the compound chassis web.

In the finished pant-type article, there will be a gap between the two elastic webs which gap is bridged by the nonwoven web. This portion of the compound chassis web will form a crotch panel in the article and the elastic panel web portions on either side of the central part of the nonwoven chassis web will form elastically extensible front and rear panels. The central nonwoven chassis web can be an elastic or non-elastic web but is preferably a non-elastic web.

The elastic webs used for forming the elastic panels in the pant-type articles may be made from different materials and may differ in one or several aspects such as in basis weight, composition, number of layers, breathability, elastic properties, tensile strength, etc.

In a further embodiment, an elastic panel web may be joined along only one side edge of a nonwoven chassis web, thus forming a pant-type article having an elastic body panel only at the front or at the rear of the article. It is also conceivable to use a full-width stretched elastic panel web to create a chassis structure having an elastic web extending also through the crotch portion of the article.

Leg elastic members can be, in particular embodiments, attached to the compound chassis web formed by the disclosed process.

The leg elastic members may be covered with a nonwoven web that is incorporated in the compound chassis web.

The chassis compound web may be provided with an elastic waist feature along at least one side edge. The elastic waist feature may be joined to the chassis component web as a separate component or may be integral with another component of the compound chassis web such as the stretched and relaxed composite elastic web.

A waist feature can be arranged at one or both edges of the compound chassis web by attaching elastic elements to the web and optionally covering the elastic elements with a nonwoven web which may be a continuous component of the chassis web or a separate nonwoven strip.

An elastic waist feature can alternatively be joined to the chassis web as a separate component that is prefabricated or is manufactured in line with the article-forming process. In particular embodiments, the elastic waist feature is continuously joined to or arranged on the compound chassis web and may be supplied as an elastic band, of any suitable kind, such as elastic laminates, elastic foam strips, elastic nonwovens, non-elastic materials that have been elasticised with elastic threads or strings, etc. A commonly used elastic waist feature is made by attaching elastic elements such as threads, bands or strings in a pre-tensioned state between two layers of nonwoven non-elastic material. All commonly used elastic materials such as natural or synthetic rubber, elastic foam, etc. can be employed. A waist feature of this type may be formed from two separate layers of nonwoven or may be made from a single layer of nonwoven that is folded into a two-layer structure. It is also possible to use the activated stretched and relaxed elastic laminate to create an elastic waist feature.

The elastic waist feature in the finished pant-type article will have a higher elastic tension than front and rear elastic panel portions produced as disclosed.

The elastic waist feature may be an integral part of a component of the compound chassis web. In this embodiment, the elastic waist feature may be formed by folding an edge portion of an elastic or non-elastic part of the compound chassis web and attaching elastic elements between the folded portions of the compound chassis web. The elastic waist feature may be formed by folding a portion of a nonwoven chassis web component that is an extension of a nonwoven layer in an elastic laminate used in the method. Elastic elements may alternatively be attached to a layer of the compound chassis web and the elastic elements may be left uncovered, or covered by a separate web. If the elastic waist feature incorporates a composite elastic web, the web may be folded to create a double laminate portion having higher elastic retraction force than the non-folded portion of the part of the chassis web including only a single-ply composite elastic web. The folded composite elastic web may be supplemented by additional elastic elements.

The method may further include any conventional production steps. Such production steps may include arranging raised elasticated or non-elasticated barriers on the chassis web and/or affixing fastener components to the chassis web.

The pant-type article produced with the method includes a chassis structure having one or more elastic panels formed from a stretched and relaxed composite elastic web. Such elastic panels may include one or more of: a front panel, a rear panel, side panels, a crotch panel and front and back waist panels arranged at the front and rear panels, respectively, and forming a waist-band on the absorbent article.

A pant-type article having elastic side panels will normally have been produced in the lengthwise direction, meaning that the length direction of the articles coincides with the MD.

The elastic chassis portions may, in particular, form at least a front and a rear panel in the absorbent article. However, it is possible to make only parts of the respective front and rear panels of a stretched and relaxed elastic panel web. In such embodiments, at least 20%, preferably at least 25%, more preferably at least 30% and most preferably at least 40% of the total surface area of the chassis includes a stretched and relaxed elastic web. As an example, the stretched and relaxed elastic web may be applied only to those parts of the front and rear panels that are intended to lie over the wearer's hips, and thus form elastic side panels Non-elastic fibrous nonwoven webs useful for making the chassis structure may include thermoplastic fibers. The nonwoven webs will generally be incorporated in joins and seams in the disposable article. Hence, it is highly desirable that the nonwoven webs be weldable by heat or by ultrasonic welding processes. Examples of suitable polymers for use in the nonwoven webs are polyethylene, polyesters, polypropylene and other polyolefin homopolymers and copolymers. The nonwovens may include mono- bi- or multicomponent fibers and blends of different kinds of fibers. The weldable nonwoven webs have a high content of thermoplastic fibers and contain at least 50% thermoplastic fibers and preferably at least 80% thermoplastic fibers.

A suitable type of nonwoven webs is creped nonwovens. Creped nonwovens generally have greater extensibility and flexibility than non-creped nonwovens. By choosing a creped nonwoven when making a three-layer nonwoven-film-nonwoven elastic laminate, it is possible to achieve a final three-layer laminate in the panty-type article that is more conformable and extensible than is possible with a non-creped nonwoven. A creped nonwoven layer makes it easier for the laminate to contract after elongation, thus increasing the elasticity when compared to a corresponding laminate including only non-creped nonwoven layers.

Elastic films for use in the articles particularly in elastic laminates include at least one nonwoven layer and one elastic film layer formed from any suitable elastic polymer or polymer blend including natural or synthetic polymers or polymer blends. Some examples of useful materials for the elastic layer are low crystallinity polyethylenes, metallocene-catalyzed low crystallinity polyethylenes, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. In particular embodiments, the elastic layer is an apertured elastic film. The elastic layer may have a basis weight of between 10 and 120 g/m$^2$, preferably between 15 and 60 g/m$^2$. One example of a suitable elastic film is an apertured three-layer elastomeric film with the composition polyethylene-styrene/ethylene/butadiene/styrene-polyethylene (PE-SEBS-PE).

The two-layer elastic pre-laminates produced by the method in WO 2007/133146 include at least one layer of fibrous material and an elastic layer. The fibrous layer is chosen so that it provides a soft and cloth-like feel and appearance to the laminate. Examples of suitable materials are meltblown webs, spunbond materials, and creped nonwovens, as set out above. Such materials are also suitable for the further nonwoven layer to which the two-layer laminate is attached. However, any soft, flexible and particularly extensible nonwoven materials and nonwoven laminates may be used, such as Spunbond-Meltblown-Spunbond-laminates (SMS), carded and spunlaced materials.

The basis weight of the nonwoven webs used in the laminates contemplated herein is suitably from 10-80 g/m$^2$ and preferably from 13-50 g/m$^2$. Examples of suitable polymers used in the fibrous materials are polyethylene, polyesters, polypropylene and other polyolefin homopolymers and copolymers. Natural fibers, for example cotton, may also be used as long as they provide the desired properties. A mixture of polymers can contribute to a higher flexibility of the nonwoven layer and thereby give the nonwoven material a higher elongation at maximum load. A mixture of polyethylene and polypropylene polymers has proven to provide good results in this respect. However, nonwovens having different fiber mixtures may also be used.

An elastic laminate can, for instance, be manufactured and activated according to the methods disclosed in WO 03/047488, WO 2007/133146 or EP 0 714 351 by applying a nonwoven web to one side of the film. The nonwoven web and the film may be extrusion bonded or may be bonded by adhesive. The thus produced laminate is then incrementally stretched to activate the elasticity of the film layer. Incremental stretching can be made to a point below the elongation at peak load of the nonwoven web to retain some strength in the nonwoven web. Alternatively, the stretching may be carried out so that the nonwoven is completely torn, as disclosed in WO 03/047488. Stretching of the laminate causes the laminate web to be necked-in in the cross-machine direction, CD.

BRIEF DESCRIPTION OF THE DRAWINGS

Embodiments of the invention will in the following be described in greater detail with reference to the appended drawings, wherein.

DETAILED DESCRIPTION

Figure 1:
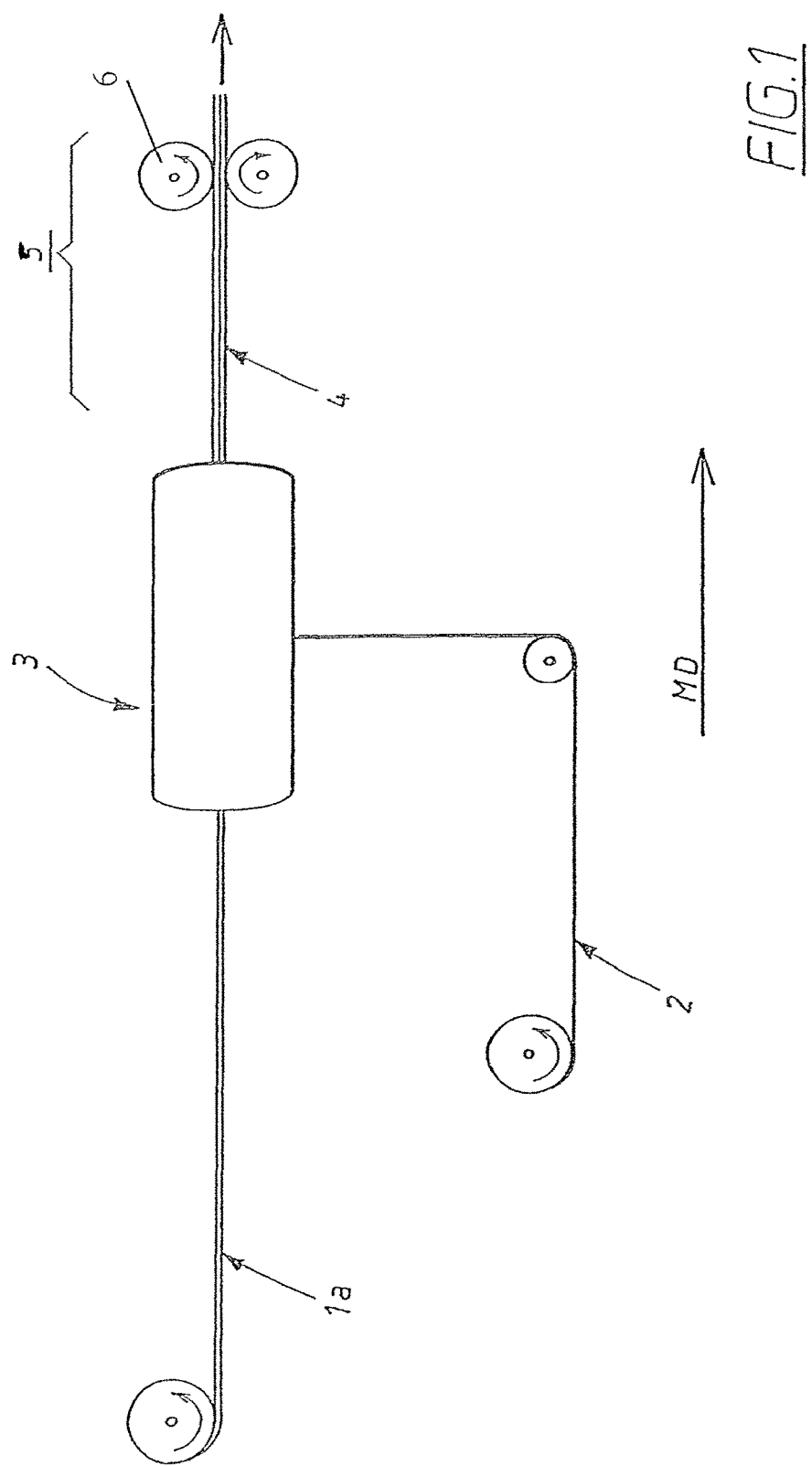
FIG. 1 shows schematically a method for producing an elastic three-layer laminate.

FIG. 1 shows schematically a method for producing an elastically stretchable three-layer laminate that can be incorporated in an absorbent article such as a pant-type article.

A bi-layer laminate elastic web 1a and a nonwoven web 2 are fed into a stretch and bonding unit 3 where the bi-layer laminate elastic web 1a is stretched by increasing the speed of the bi-layer laminate elastic web 1a in the machine direction (MD) in one or more steps by running the elastic web between rollers driven at different speeds. The nonwoven web may be stretched by a small amount such as by up to 5% of its initial length in order to improve control of the web in the process. The stretched bi-layer laminate elastic web 1a is subsequently bonded to the nonwoven web 2 in the stretch and bonding unit 3. The bi-layer laminate elastic web 1a includes a nonwoven layer and an elastic film layer and may be a stretch-activated laminate of a non-elastic nonwoven web and an elastic film that has been rendered elastic by stretching the nonwoven web as herein described. The nonwoven web 2 is bonded to the film-side of the bi-layer laminate elastic web 1a resulting in a tri-layer laminate 4 including an elastic film that is sandwiched between two nonwoven layers.

Bonding of the bilayer laminate elastic web 1a to the nonwoven web 2 may be made in any suitable manner such as by coating, spraying or meltblowing adhesive to one or both abutting surfaces of the bilayer laminate elastic web 1a and the nonwoven web 2 before passing the webs through a bonding nip. The adhesive can, in particular embodiments, be a thermoplastic hot-melt adhesive. Other types of adhesive may also be used, if desired.

Thermobonding techniques can also be used, such as heat bonding between heated rollers or ultrasonic bonding. The amount of bonding between the webs may be adjusted by adjusting the amount of binder that is used or by selecting a suitable bond pattern and bond distribution in order to obtain sufficient bonding between the webs to avoid delamination.

The tri-layer laminate 4 is then passed through a relaxation area 5 involving relaxation in at least one step where the speed of the tri-layer laminate 4 is reduced in the MD by passing the tri-layer laminate 4 between at least one pair of rollers 6, which are driven at different speeds.

In particular embodiments, the bi-layer laminate elastic web 1a is stretched by at least 50% of the initial non-stretched length, preferably by at least 70% of the initial non-stretched length, and more preferably by at least 90% of the initial non-stretched length in at least the MD. Depending on the elastic material, the available stretch may vary with the desire generally being to stretch the material as much as possible. The bi-layer laminate elastic web 1a may be stretched by up to 150% of the initial non-stretched length, preferably by up to 300% of the initial non-stretched length and most preferably by up to 500% of the initial non-stretched length. In the relaxation step, the elastic tri-layer laminate 4 including the stretched elastic bi-laminate is relaxed in the MD by at least 4% of the stretched length of the bilayer laminate elastic web 1a, preferably relaxed by 4-50% of the stretched length of the stretched elastic panel web, more preferably by 4-20% of the stretched length of the stretched elastic panel web and most preferably by 4-10% of the stretched length of the stretched elastic panel web.

Figure 2:
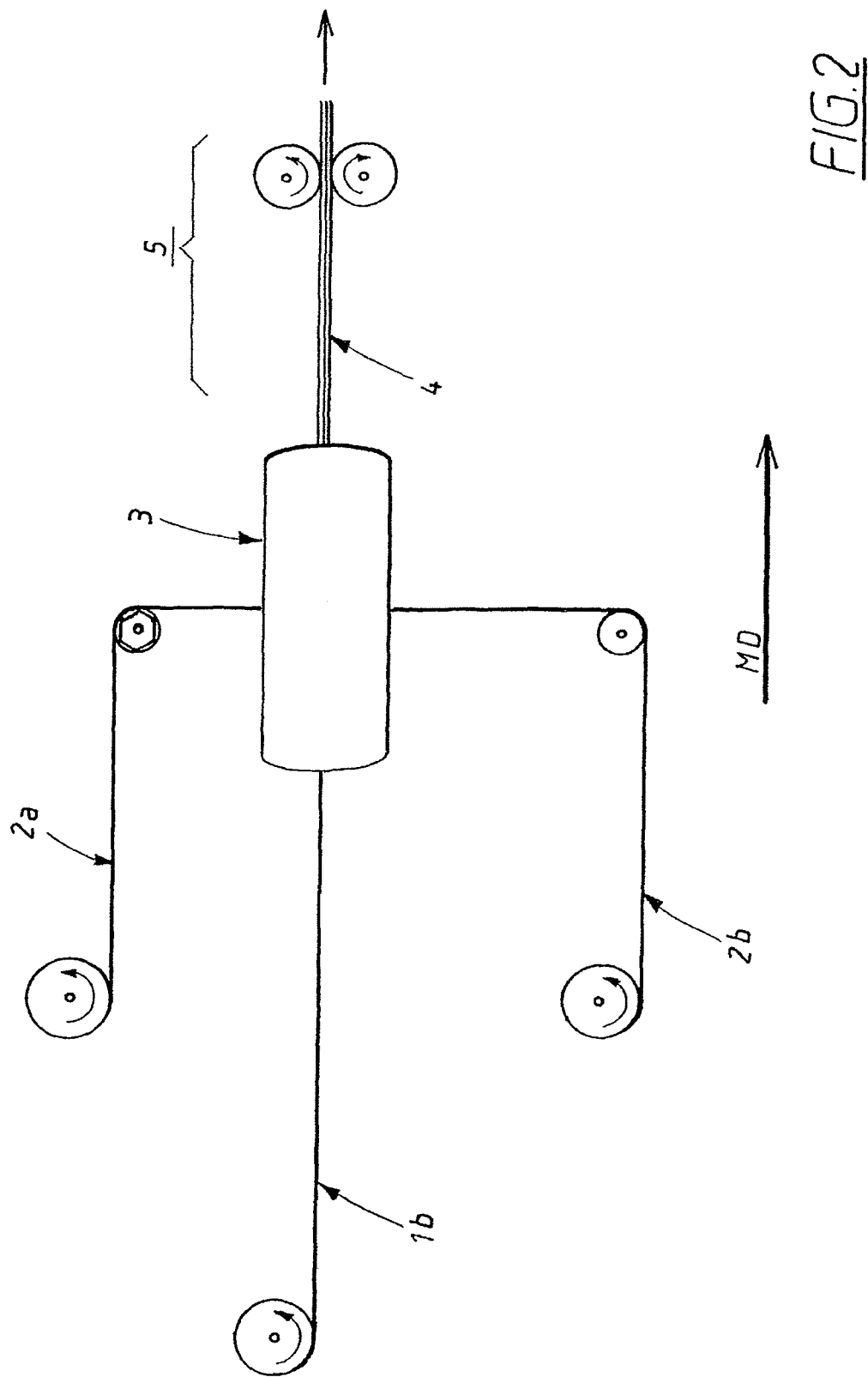
FIG. 2 shows schematically an alternative method for producing an elastic three-layer laminate.

FIG. 2 shows an alternative way of producing a tri-layer laminate 4 from an elastic film web 1b and first and second nonwoven webs 2a, 2b. The first and second nonwoven webs 2a, 2b and the elastic film web 1b are fed in the MD into a stretch and bonding unit 3 optionally while being stretched by up to 5%. In the stretch and bonding unit 3, the elastic film web 1b is first stretched in at least one step as described with reference to FIG. 1. The stretched elastic film web 1b is subsequently bonded to the nonwoven web 2a,2b in the stretch and bonding unit 3. The nonwoven webs 2a, 2b are bonded to opposing surfaces of the elastic film web 1b resulting in a tri-layer laminate 4 including an elastic film that is sandwiched between two nonwoven layers.

The tri-layer laminate 4 is then passed through a relaxation area 5 and relaxed in the same manner as the tri-layer laminate in FIG. 1.

The stretching and relaxation steps of the invention have been described in connection with three-layer elastic laminates but may equally well be performed on elastic laminate webs including only two layers or more than three layers.

Figure 3:
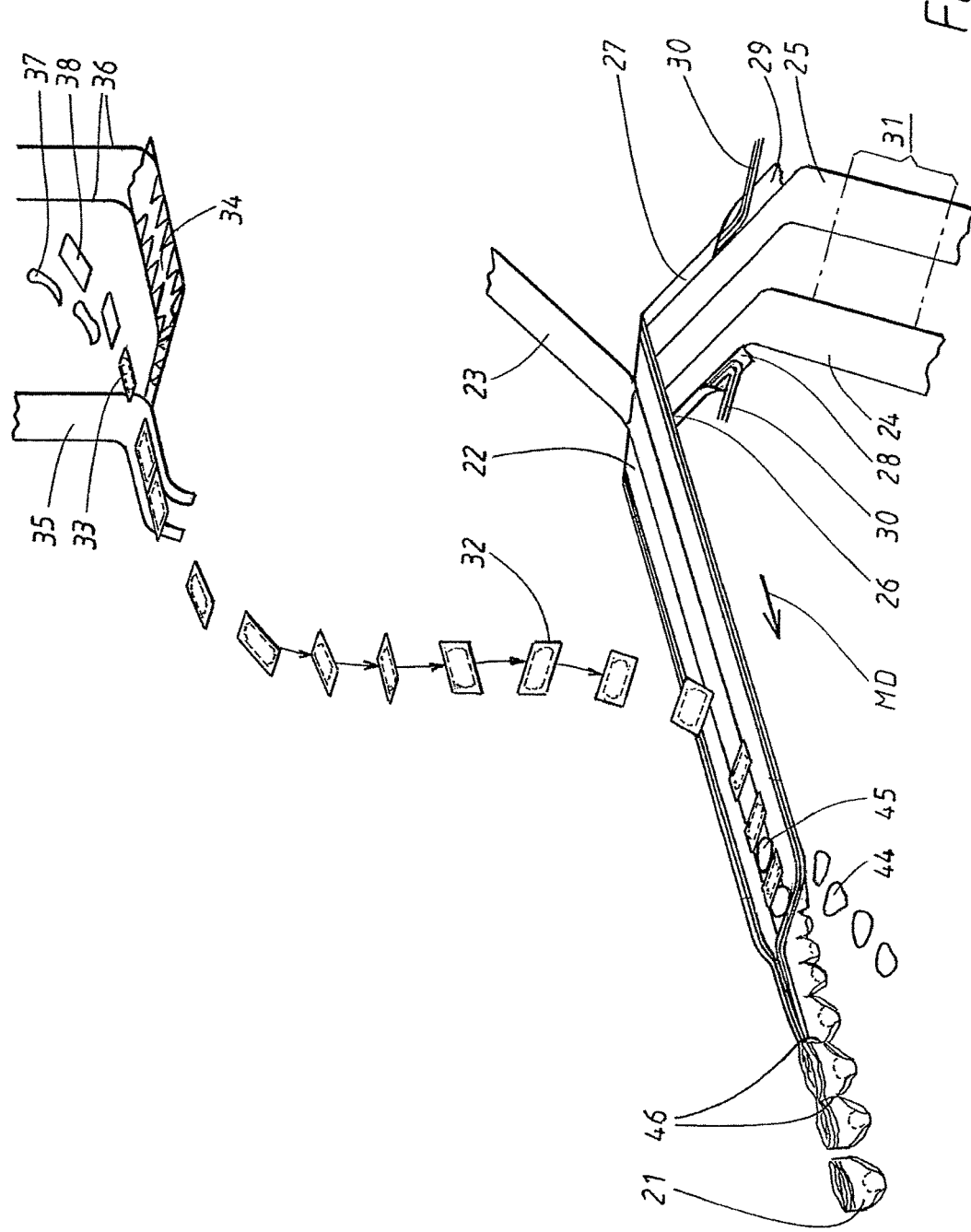
FIG. 3 shows a schematical representation of a method for producing pant-type absorbent articles in accordance with an embodiment of the invention.

FIG. 3 shows schematically a method for producing pant diapers 21 or other pant-type articles. The process in FIG. 3 is a direct continuation of a stretching/bonding/relaxation process such as those shown in FIGS. 1 and 2. In accordance with an embodiment of the invention, the method involves forming a chassis structure that may carry a core component. In the shown embodiments, a core component is formed separately as a "core pack", with an absorbent core enclosed between a topsheet and a liquid impermeable backsheet. This is one particular way of incorporating a core component in the chassis structure of a pant-type absorbent article. However, alternative embodiments utilizing parts of the chassis structure as topsheet and/or backsheet are also contemplated. The pant-type article may be a non-absorbent article that may be used to carry a separate absorbent insert.

Particular embodiments of the process involve using continuous webs of material to form different chassis web portions such as a crotch portion, front and back panel portions and a waist band portion, and stretching the elastic panel webs in the machine direction, MD, as shown in the Figures. However, as previously stated, the process may also involve the incorporation of discrete elastic panel webs and other elements and may involve stretching the elastic panel webs in the cross direction, CD, or in more than one direction.

As shown in FIG. 3, multiple chassis structures are formed from a compound chassis web 22 including a central nonwoven chassis web 23, first and second composite elastic webs 24,25 and first and second waist features 26,27. The elastic composite webs 24,25 can be the tri-layer laminate webs 4 produced as shown in the methods in FIG. 1 or 2. Alternatively, the webs may be any other composite elastic webs as herein disclosed. The composite elastic webs include at least one layer of an elastic material such as an elastic film or an elastic nonwoven and at least one further layer that may be elastic or non-elastic.

Before joining the composite elastic webs 24,25 to the central nonwoven chassis web 23, the composite webs are passed through a relaxation area 31 where they are relaxed at least in the machine direction (MD) by at least 4% of their stretched length. The relaxation step is performed as described with reference to the processes in FIGS. 1 and 2. Accordingly, the process shown in FIG. 3 overlaps slightly with and follows directly on a process such as those described with reference to FIGS. 1 and 2.

Waist features 26,27 are created after the relaxation step by joining separate nonwoven strips 28,29 to the outer edges of the relaxed composite elastic webs 24,25, attaching elastic elements 30 to the nonwoven strips 28,29 and folding and securing the nonwoven strips 28,29 over the elastic elements 30 to create elastic waistbands along the edges of the compound chassis web 22.

The elastic waist features may alternatively be formed by folding an edge portion of one or both of the relaxed composite elastic webs 24,25. The folded portion will have greater elastic force than a non-folded web. If desired, the folded laminate web may be supplemented with additional elastic elements. It is also possible to create a waist feature at the edge of one or both of the composite elastic webs

24,25 by attaching elastic elements to the web and optionally covering the elastic elements with a separate nonwoven strip.

An optional core pack or core component 32 is produced separately from the pant-forming process and is laid down on the compound chassis web 22.

The core component 32 includes an absorbent core 33 arranged between a liquid barrier layer 34 and a liquid pervious topsheet layer 35. In the shown example, the core component 32 further includes elastic elements 36 arranged in curve-shaped patterns on the liquid barrier layer 34. The shown pattern is only intended as an example and other patterns may be used for the elastic elements 36 such as linear elastic elements. It is also possible to dispense with elastic elements in the core component 32 altogether. The absorbent core is shown as a two-component structure with an upper, smaller absorbent layer 37 and a lower somewhat larger layer 38. It is to be understood that the construction of the core component 32 and the absorbent core is by no means limiting for the invention. Hence, any commonly employed core concepts and materials may be used in the process.

Moreover, by using nonwoven materials having thermoplastic properties in the composite elastic webs, the webs can be joined to other components by thermo-bonding and ultrasonic welding techniques. For example, it may be beneficial if at least one of the nonwoven layers in a three-layer laminate nonwoven-film-nonwoven laminate is substantially or completely made of thermoplastic fibers, in particular, polypropylene fibers. The nonwoven layer can then be used to form side seams with good tensile strength. The side seams can be, in particular, breakable side seams, i.e. welds that may be readily peeled or torn apart when the pant diaper is removed.

The method shown in FIG. 3 does not include the application of leg elastic elements. However, it is of course possible to apply leg elastic if additional elastification is needed at the leg openings of a pant-type absorbent article. Leg elastic may be applied in any manner and using any elastic elements. One example of a suitable method of arranging leg elastics is disclosed in WO 2004/078083.

As shown in FIG. 3, the relaxed elastic panel webs 24,25 are joined to the central nonwoven chassis web 23. The embodiment shown in FIG. 3 may alternatively involve relaxing a stretched and bonded composite elastic web as shown in FIGS. 1 and 2, and subsequently cutting the web into two web halves forming the composite elastic webs 24,25 shown in FIG. 3.

After the central nonwoven chassis web 23 has been joined to the relaxed composite elastic webs 24,25, a portion 44 is cut out from the compound chassis web 22 between the core components 32 to create leg openings 45. The compound chassis web and the integrated core components 32 are then folded centrally and the web halves are joined in side seams 46 between the core components. Finally, individual pant diapers 21 are cut from the production web.

The method in FIG. 3 shows the core components being joined to the chassis web before forming the leg openings 45. However, in an alternative method, the core components 32 may be joined to the chassis web after the leg cut-outs 44 have been made.

Figure 4:
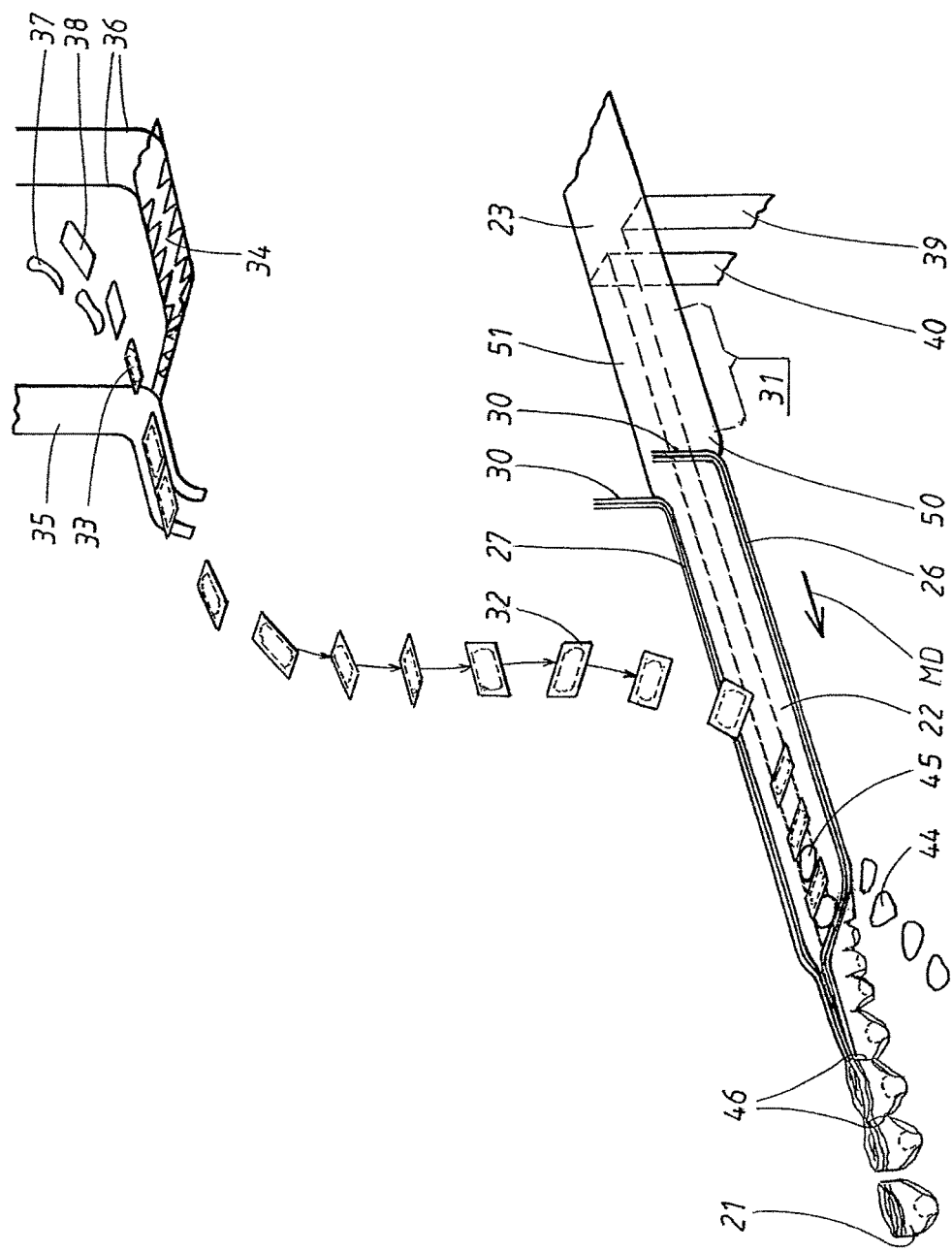
FIG. 4 shows a schematical representation of a second embodiment of a method for producing pant-type absorbent articles in accordance with an embodiment of the invention.

In the method in FIG. 4, a central nonwoven chassis web 23 that may be elastic or non-elastic extends in the cross direction (CD) over the full width of the compound chassis web 22.

Waist features 26,27 are formed in the compound chassis web 22 by attaching elastic elements 30 on edge portions 50,51 of the chassis web and folding and securing the edge portions 50,51 over the elastic elements 30. The direction of folding of the edge portions 50,51 is not critical to the invention. However, one particular method is that the edge portions 50,51 be folded in the direction shown in FIG. 3, since the free edges of the folded edge portions 50,51 will then be on the inside of the resultant pant-type article 21 and the outside of the pant-type article 21 will have a smoother and more tailored appearance.

The composite web formed by bonding first and second elastic webs 39,40 to the central nonwoven web 23 is passed through a relaxation area 31 before forming the waist features 26,27 and adding further components to the compound chassis web 22.

The first and second elastic webs 39,40 are, in particular embodiments, bi-laminate webs that are joined while being held in a stretched state to the central nonwoven chassis web 23. If the stretched elastic webs 39,40 are bi-layer film/nonwoven laminates such as the bi-layer laminate 1*a* shown in FIG. 1, the bi-layer laminates 39,40 are bonded to the central nonwoven chassis web 23 with the nonwoven side facing away from the central nonwoven chassis web 23 and with the film side facing towards the central nonwoven chassis web 23 so that the elastic film layer is sandwiched between the nonwoven layers. The stretched elastic webs 39,40 are arranged along the edges of the chassis web 23, leaving a central portion of the central nonwoven chassis web 23 free from the stretched elastic webs 39,40. In an alternative embodiment, the elastic two-layer laminate webs may be applied as a single web having no central gap. Such an embodiment produces an article having an elastic three-layer laminate covering the chassis web crotch portion, as well as the chassis web front and back panel portions.

When applied as shown in FIG. 4, the elastic webs 39,40 will end up on the outside of the finished pant-type article 21. However, it is of course possible to arrange the laminate webs on the inside of the chassis web 23, so that the central nonwoven chassis web 23 forms a continuous outer surface on the finished pant-type article 21.

Before incorporation in a compound chassis web, the first elastic webs are stretched at least in the MD by at least 50% of their initial non-stretched length, preferably by at least 70% of their initial non-stretched length and most preferably by at least 90% of their initial non-stretched length. The maximum stretch is determined by the properties of the particular elastic material that is used. Accordingly, the stretch may be up to 150% of the initial non-stretched length, preferably up to 300% of the initial non-stretched length and most preferably up to 500% of the initial non-stretched length. The elastic webs 24,25, 39,40 used in the methods of FIGS. 3 and 4 to form front and rear elastic panels in a pant-type article need not be stretched to the same extent if different elasticity is desired in the different panels of the finished chassis structure. Likewise, it is possible to use elastic webs having different compositions, and different elastic properties, etc.

The core components 32 are laid down on the assembled compound chassis web 22 as shown in FIG. 4, leg cut-outs 44 are made to form leg openings 45, the compound chassis web 22 is folded together with the core components 32, side seams 46 are formed and the individual pant diapers 21 are severed from the production web in the same manner as in the FIG. 3 process.

Leg elastic (not shown) may be applied to the compound chassis web 22 for instance in a sinus curve pattern. The leg elastic can be any conventionally used elastic element such as one or more elastic threads, bands, etc. One suitable way of arranging leg elastic on a chassis web is disclosed in WO 2004/078083.

Figure 5:
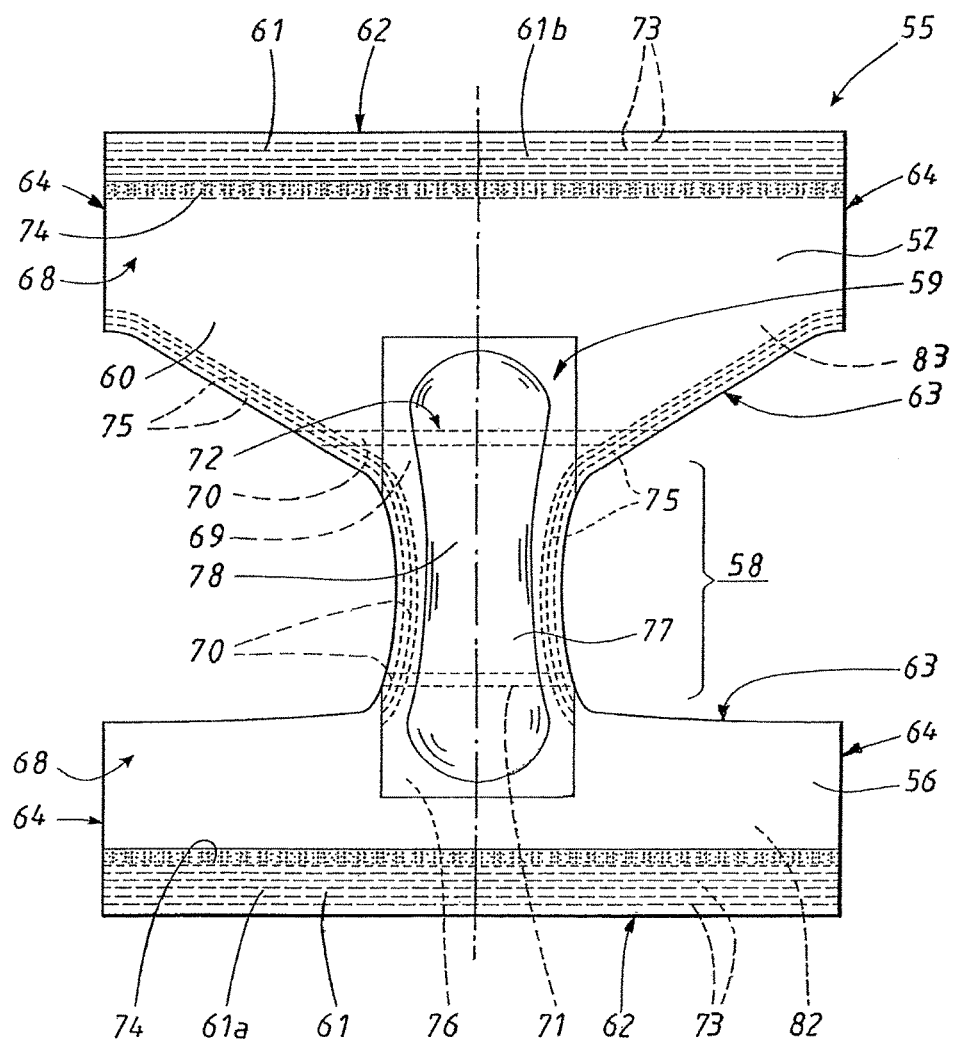
FIG. 5 shows a pant-type diaper in accordance with an embodiment of the invention in a flat state.
Figure 6:
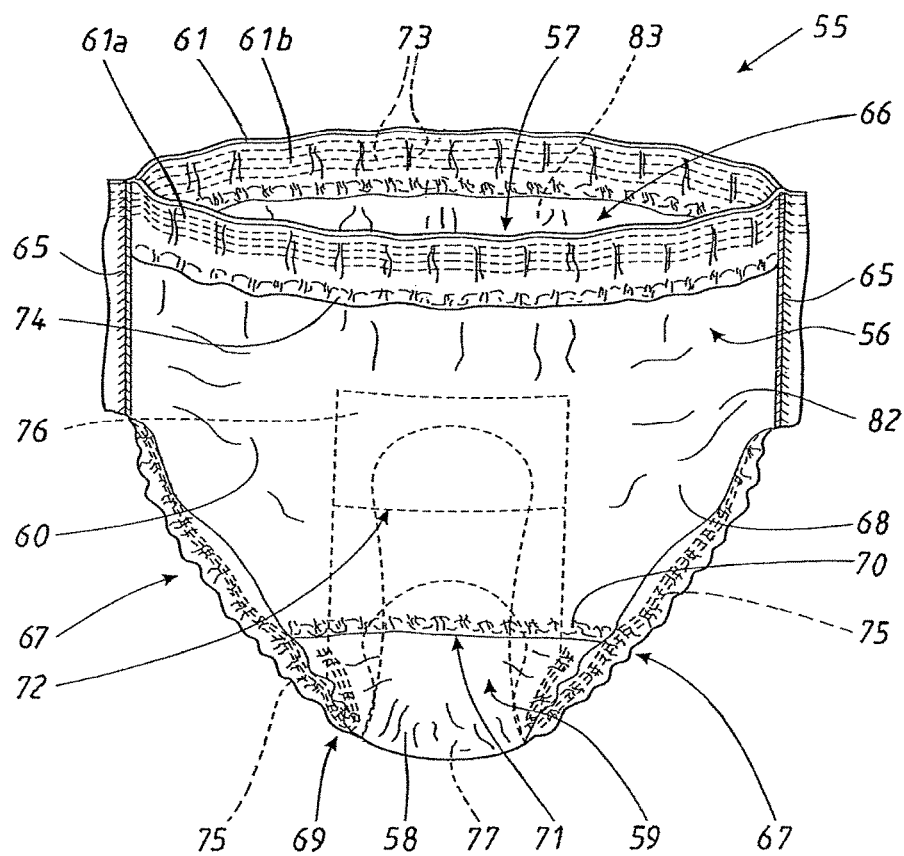
FIG. 6 shows the diaper in FIG. 5 with closed side seams.

As an illustrative example of an absorbent article that can be produced by the disclosed method, FIGS. 5 and 6 show a pant-type diaper.

The pant-type diaper 55 in FIGS. 5 and 6 is designed to enclose the lower part of a wearer's trunk in the manner of conventional underwear. In FIG. 5, the diaper 55 is shown from the inside, i.e. from the side facing the wearer when the article is worn and in FIG. 6, the diaper is shown from the outside, or the garment-facing side, which is the side that is facing away from the wearer when the diaper is worn.

The diaper has a front panel 56, a back panel 57 and a crotch panel 58 extending between the front and back panels 56,57 and having a relatively narrow width as compared to the front and back panels 56,57. The front and back panels 56,57 are arranged to cover the wearer's hips and to extend over the belly and the back of the wearer to encircle the lower part of the wearer's trunk.

The diaper 55 further includes a core region 59 extending from the crotch panel 58 into the front panel 56 and the back panel 57. The front and back panels 56,57 form part of a chassis 60 that extends on the garment-facing side of the diaper 55 and covers and surrounds the core region 59. The chassis 60 includes the front panel 56, the back panel 57 the crotch panel 58 and an elastic waist panel or waist band 61 secured to the front and back panels 56,57. Each of the front and back panels 56,57 has a waist edge 62 a crotch edge 63 and a pair of side edges 64 respectively.

The term "panel" is used herein to denote a delimited functional part of the diaper chassis while the terms "region" and "portion" are used to denote the location of a particular component of the diaper in the chassis or to describe the intended positioning of a particular part of the diaper in relation to a user's body. A panel may be a separate component or an integrated part of the chassis. The panels are contiguous parts of the chassis that do not overlap with each other. A region or portion may have an extension fully or partially coinciding with one or more panels.

When components are attached, bonded, affixed, fixed or secured to each other they are separate parts that have been bonded by any suitable means such as adhesively, by stitching or by ultrasonic welding or thermo-welding. The above terms also cover separable (openable) joins, such as separable side seams and reclosable joins such as hook- and loop joins, reclosable tape joins, snap fasteners, etc. The term joined as used herein additionally covers components that are in a side-by-side configuration and are connected by a common layer or element. Components that have been arranged on each other need not be bonded, although as used herein, the term "arranged" should be broadly interpreted to also include bonded components.

The front and back panels 56,57 are joined to each other along their side edges 64 by thermobonding, ultrasonic welding, glue strings or the like to form side seams 65, as shown in FIG. 6. The elastic waist band 61 includes a front waist panel 61a and a back waist panel 61b, which are secured to the front panel 56 and the back panel 57, respectively. The front and back waist panels 61a, 61b are also joined to each other along the side seams 65. By joining the front and back panels 56, 57 and the waist panels 61a, 61b, the pant diaper 55 is provided with a waist opening 66 and a pair of leg openings 67.

FIG. 5 shows the diaper 55 in a flat state with any elastic components that are attached to the chassis 60 under tensional stress drawn out to the full non-tensioned dimensions of the chassis 60. FIG. 6 shows the pant diaper 55 as it appears when the side seams 65 have been formed and the tensioned elastic elements have been allowed to relax and gather the chassis material to form elasticized leg and waist openings 67,66.

The front and back panels 56,57 are constituted by an elastic panel web 68 that has been activated and stretched by 75-300%, preferably by 90-150% and most preferably by 100-120% in the width-wise direction of the diaper, and subsequently relaxed from the stretched state by 4-10% of the stretched length before being joined to further components in the diaper chassis. The front and back panels 56,57 are preferably elastically stretchable at least in the width-wise direction which is the direction of the waist edges 62. The front and back panels 56,57 may additionally be elastically stretchable perpendicular to the waist edges 62, in the direction of the side edges 64. Each of the front and back panels 56,57 comprise a stretched elastic panel web 82,83.

The crotch panel 58 is formed from a nonwoven crotch material 69 that has been joined to the front and back panels 56,57 at crotch seams 70. Hence, the crotch material 69 which preferably is a non-elastic material, such as a non-elastic nonwoven material, is arranged in the core region 59 of the article and overlaps slightly with the elastic front and back panels 56,57. The crotch material 69 is joined along its transverse edges 71,72 to the front and back panels 56,57 at the overlapping portions. The joining can be made in any suitable way such as by ultrasonic welding, adhesively or similar. In alternative embodiments, an outer nonwoven material may extend continuously over the front and back panels 56, 57 and the crotch panel 58 so that no seams or joins are needed between the panels 58,56,57.

In the shown example, the elastic waist band 61 includes first and second plies of substantially non-elastic nonwoven material that is elasticized by one or more elongate elastic members 73, such as elastic threads or bands. The first and second plies can be formed from a single layer of material that is folded over onto itself or can be made from two separate strips of material. The elastic members 73 are arranged in the waist band 61 in a tensioned state such that they contract and gather the nonwoven material in the waist band 61 when they are allowed to relax, as shown in FIG. 7.

The elastic waist band 61 is secured to the front and back panels 56,57 with the elastic members 73 in an extended state and with the material in the front and back panels sandwiched between the nonwoven plies in the waist band. Alternatively, the elastic waist band 61 can be a component that is prefabricated and joined to the outside or the inside of the front and back panels 56,57 respectively. The waist band join 74 between the waist band 61 and the front and back panels 56,57 can be made in any suitable way such as by means of ultrasonic welding, heat welding, or adhesively. A further option is to create the waist band 61 from one or more non-elastic nonwoven layers that are also parts of the front and back panels 56,57 and form continuous extensions thereof. It is also conceivable to form an elastic waist feature by double-folding portions along the waist edges 62 of the elastic front and back panels 56,57 and optionally supplementing the folded portions by additional elastic elements.

Elastic members 75 are also arranged at the edges of the leg openings 67 and serve to elasticize the leg openings. The elastic members at the leg openings can be any kind of conventional elastic elements such as elastic threads, bands, foam strips, or similar.

The planar extension of the core region 59 is defined by a liquid-impervious barrier sheet 76 arranged between an absorbent core 77 and the chassis 60. The liquid-impervious barrier sheet 76 has rectangular shape and the absorbent core 77 is hour-glass shaped. A liquid permeable topsheet 78 is arranged over the core 77 and the liquid-impervious barrier sheet 76. Hence, the liquid-impervious barrier sheet 76 underlies the absorbent core 77 and the adjacent areas immediately outside the absorbent core 77.

The liquid-permeable topsheet 78 can include any material known for the purpose, such as a layer of nonwoven material, a perforated plastic film, net material, tow, or the like. The topsheet 78 can, of course, also include a laminate of two or more sheets of the same or different material.

The liquid-impervious barrier sheet 76 can include a liquid-impermeable plastic film, a nonwoven sheet which has been coated with a liquid barrier material, or some other flexible material sheet which has the ability to withstand liquid penetration. However, it can be advantageous if the liquid-impervious barrier sheet 76 is breathable, i.e. permits the passage of water vapor through the sheet 76.

The absorption core 77 can be made up of absorbent material, such as cellulose fluff pulp, tissue, absorbent foam, etc. It is also possible for the absorption core to contain superabsorbents, i.e. polymer materials which are able to absorb body fluid corresponding to many times their own weight and form a hydrogel. Such superabsorbents are usually present in the form of particles, but fibers, flakes, granules and films are also available. Moreover, the absorption core 77 can include non-absorbent components such as stiffening elements, shaping elements, binders, etc. Various types of liquid-receiving porous structures such as fiber wads, open-cell foam or the like can also be included in the core.

The topsheet 78, barrier sheet 76 and absorption core 77 can be produced as a separate component or "core pack" that is subsequently integrated in the diaper chassis as shown in FIGS. 2-5. The various components included in the core pack can be connected to one another in a conventional manner, for example by adhesive bonding, ultrasonic welding or thermowelding. The core pack can of course contain further components in addition to those described here, for example the core pack can include a liquid transport sheet, elastic members, shape-stabilizing members, shaping elements or the like.

In the embodiment shown in FIGS. 5 and 6, the core pack has been integrated with the chassis after the chassis has been fully assembled. Alternatively, the core pack can be applied to the chassis before the chassis is completely assembled.

The nonwoven material 69 in the crotch panel 58 is arranged on the garment-facing side of the liquid-impervious barrier sheet 76. The core region 59 extends into the front and back panels 56,57 so that the elastic webs 68 in these panels overlap with the liquid-impervious barrier sheet 76 in the outer parts of the core region 59 as seen in FIG. 3. The elastic web 68 is arranged on the garment-facing side of the liquid-impervious barrier sheet 76.

As shown in FIGS. 5 and 6, an elastic web 68, in particular embodiments, forms the front and the back panels 56,57 of the pant diaper 55. However, it is possible to make only parts of the respective front and back panels 56,57 of the elastic web 68. In such embodiments, at least 20%, preferably at least 25%, more preferably at least 30% and most preferably at least 40% of the total surface area of the chassis as seen in the flat state shown in FIG. 5 is constituted by an elastic web that has been stretched and relaxed. As an example, the elastic web may be used only in those parts of the chassis that are intended to lie over the wearer's hips and thus form elastic side panels. It is also possible to design a pant article without any overlap between the core region 59 and the elastic laminate material in the front and back panels 56,57.

A considerable advantage with an absorbent article produced as disclosed and having at least one elastic panel produced as disclosed is that the same article will fit wearers within a broader size range than an article produced with identical materials and using a method differing only in that the relaxation step after the stretching step has been omitted. This is due to the fact that an elastic panel produced with the method as disclosed provides the absorbent article with greater extensibility in the panel area than an elastic panel produced with previously known stretch-bonding methods.

The disclosed and shown processes in FIGS. 1-4 should be understood as only being examples of the method. Hence, the different method steps may be carried out in different order from that described, as explained above. Moreover, the method covers all embodiments wherein a stretched and relaxed composite elastic web is introduced in a process for forming an absorbent article and incorporated as a part of a compound chassis web. Accordingly, the composite elastic web may be used to elasticise any portion of the compound chassis web, such as the crotch panel portion, the front and/or back panel portion, and the waist panel portions. One or more stretched and relaxed composite elastic panel webs may be introduced in the process. The compound nonwoven chassis web to which the activated stretched and relaxed elastic laminate web is laminated may have portions that are not elasticised by the activated stretched and relaxed elastic web. Such non-elasticised portions of the compound chassis web may be used to form a waist feature, a non-elastic crotch panel portion, non-elastic portions in registry with the absorbent core component, etc.

The process may include application of further components such as elasticised or non-elasticised barriers, lotion, odor control agents, shaping elements, stabilising elements, fasteners, etc.

Elasticity Test

The method measures how an elastic material behaves at cycles of repeated load and unload. The sample is stretched to a predetermined elongation and a cyclic movement between 0 and the predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

Crosshead speed: 500 mm/min
Clamp distance: 50 mm
Preload: 0.05 N

The sample is placed in the clamps according to the marks and it is made sure that the sample 1 centered and fastened perpendicularly in the clamps. The tensile tester is started and three cycles between 0 and the predetermined elongation equal to the highest defined 1st load are performed. Before the last cycle, the sample is relaxed for 1 minute, then the permanent elongation is measured by stretching the sample until a force of 0.1 N is detected and the elongation is read.

An elastic material is defined as a material having a permanent elongation after relaxation of less than 10% after the material has been subjected to an elongation of 30% in the test above. An elongation of 30% means an elongation to a length that is 30% longer than the initial length of the sample.

A non-elastic material has a permanent elongation after relaxation of more than 10% after having been subjected to an elongation of 30%.

The invention claimed is:

1. A method for producing pant-type articles having a waist-encircling portion and leg-encircling portions, each article comprising a chassis structure having at least one elastic panel, said method comprising:
   a) providing a first web being an elastic laminate web comprising a plurality of layers including at least one layer of an elastic film material and at least one nonwoven layer;
   b) stretching the first web by at least 70% of the initial non-stretched length in at least one direction to form a first stretched elastic web;
   c) laminating the first stretched web to a first edge portion of continuous nonwoven web being a component of the chassis structure;
   d) providing a second web being an elastic web comprising at least one layer of an elastic material;
   e) stretching the second web by at least 70% of the initial non-stretched length in at least one direction to form a second stretched elastic web;
   f) laminating the second stretched elastic web to a second edge portion of the continuous nonwoven web to form a composite elastic web;
   g) relaxing the composite elastic web formed by laminating the first and second stretched elastic webs to the continuous nonwoven web by 4-50% of the stretched length of the stretched elastic webs; and
   h) assembling said chassis structure from chassis components comprising the composite elastic web having the same stretched length as the composite elastic web had immediately after step g).

2. The method according to claim 1, wherein, in step b), the first web is stretched by at least 90% of the initial non-stretched length.

3. The method according to claim 1, wherein, in step b), the first web is stretched by up to 150% of the initial non-stretched length.

4. The method according to claim 1, wherein, in step c), the first stretched elastic web is bonded to the second web by adhesive that is applied to one or both webs by coating, spraying, extrusion or meltblowing.

5. The method according to claim 1, wherein, in step c), the first stretched elastic web is bonded to the second web by thermobonding by heat or ultrasonically.

6. The method according to claim 1, wherein said method is a continuous process and the first web is a continuously running web travelling in a machine direction.

7. The method according to claim 6, wherein, in step b), the first web is stretched at least in the machine direction.

8. The method according to claim 1, wherein, in step h), the chassis structure is assembled as a continuously running compound chassis web travelling in a machine direction and comprising the chassis components, and wherein the chassis structure is further processed with steps comprising:
   f) cutting the chassis structure to form leg openings,
   g) folding the chassis structure along a central fold line in the machine direction,
   h) forming side joins in the folded chassis structure, and
   i) separating individual pant-type articles from the chassis structure by severing the compound chassis web at the side joins.

9. The method according to claim 8, wherein an absorbent core component is joined to the chassis structure.

10. The method according to claim 1, wherein the elastic laminate web comprises at least one elastic film layer.

11. The method according to claim 10, wherein the elastic laminate web is a tri-layer laminate, the elastic film layer being bonded between two nonwoven layers.

12. The method according to claim 1, wherein step b) includes a combination of at least two stretching steps.

13. The method according to claim 1, wherein step g) includes a combination of at least two relaxing steps.

14. The method according to claim 8, wherein step h) comprises the following steps:
   h1) joining the elastic panel to a first edge of a continuous central nonwoven chassis web being a component of the chassis structure, and
   h2) joining a second elastic panel made in accordance with steps a) through d) to a second edge of the continuous central nonwoven chassis web.

15. The method according to claim 1, wherein the first and second stretched elastic webs comprise different materials.

16. The method according to claim 1, wherein the first stretched elastic web is stretched to a greater degree than the second stretched elastic web.

17. The method according to claim 8, wherein the chassis structure is provided with an elastic waist feature along at least one edge.

18. The method according to claim 17, wherein the elastic waist feature is joined to the chassis structure as a separate component.

19. The method according to claim 17, wherein the elastic waist feature is integral with another component of the chassis structure.

20. The method according to claim 19, wherein the elastic waist feature is integral with the elastic panel.

21. The method according to claim 8, wherein the further processing of the chassis structure comprises applying leg elastic elements to the chassis structure.

22. The method according to claim 3, wherein, in step b), the first web is stretched by up to 300% of the initial non-stretched length.

23. The method according to claim 22, wherein, in step b), the first web is stretched by up to 500% of the initial non-stretched length.

24. The method according to claim 1, wherein, in step g), the composite elastic composite web is relaxed by 4-20% of the stretched length of the first stretched elastic web.

25. The method according to claim 24, wherein, in step g), the composite elastic composite web is relaxed by 4-10% of the stretched length of the first stretched elastic web.

26. The method according to claim 1, wherein the stretched length of the elastic panel is maintained at a constant length until step h).

* * * * *